(12) United States Patent
Watanabe et al.

(10) Patent No.: US 6,822,121 B2
(45) Date of Patent: Nov. 23, 2004

(54) PRODUCTION PROCESS OF CYCLOHEXENYL KETONES

(75) Inventors: Shinya Watanabe, Kanagawa (JP); Hideo Ujihara, Kanagawa (JP); Takeshi Yamamoto, Kanagawa (JP); Toshimitsu Hagiwara, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/875,158

(22) Filed: Jun. 7, 2001

(65) Prior Publication Data

US 2002/0004615 A1 Jan. 10, 2002

(51) Int. Cl.[7] .............................................. C07C 45/67
(52) U.S. Cl. ........................................................ 568/341
(58) Field of Search ......................................... 568/341

(56) References Cited

U.S. PATENT DOCUMENTS 3,914,242 A * 10/1975 Boshagen et al. .......... 260/304
4,334,098 A * 6/1982 Mookherjee et al. ....... 568/347

FOREIGN PATENT DOCUMENTS

DE 3003894 * 8/1981

* cited by examiner

Primary Examiner—Barbara P. Badio
(74) Attorney, Agent, or Firm—Sughrue Mion, PLLC

(57) ABSTRACT

An economical process for producing (2- and/or 1-)cyclohexenyl methyl ketones which are intermediates for the synthesis of α- or β-damascone. In the presence of a catalyst, a 3-cyclohexenyl methyl ketone represented by the following formula (1a):

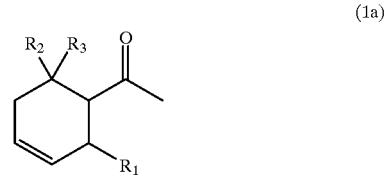

(1a)

wherein, $R_1$, $R_2$ and $R_3$ each independently represents a hydrogen atom or a methyl group and at least two of $R_1$, $R_2$ and $R_3$ are methyl groups, is isomerized.

4 Claims, No Drawings

PRODUCTION PROCESS OF CYCLOHEXENYL KETONES

FIELD OF THE INVENTION

The present invention relates to a production process of intermediate starting materials used for perfumery, more specifically, 2-cyclohexenyl methyl ketones (1b) and 1-cyclohexenyl methyl ketones (1c), or mixtures thereof.

BACKGROUND OF THE INVENTION 2,6,6-Trimethylcyclohexenyl methyl ketone is a useful compound as an intermediate for the synthesis of fruity floral fragrant materials such as α- and β-damascone. Damascones typified by α-damascone which serves as a key note component of natural roses have been commercially produced and practically used as an important fruity floral fragrance. Damascones have three double-bond-depending isomers as described below. These Isomers have their own odor notes, respectively, while they have a fruity floral note basically. They are used differently according to their application purposes.

(2a)

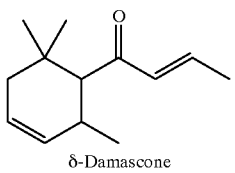

δ-Damascone (2b)

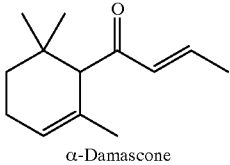

α-Damascone (2c)

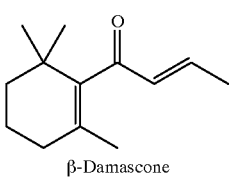

β-Damascone

A large number of production processes for these damascones {δ-damascone (2a), α-damascone (2b), β-damascone (2c)} have been reported, for example, in "Review" (Shigeru Torii, et al., Koryo, No. 125, 47–60 (1979)). Among them, a production process of α-Damascone (2b), β-Damascone (2c), δ-Damascone (2a) represented by the following reaction

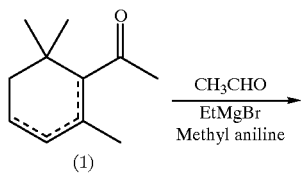

-continued

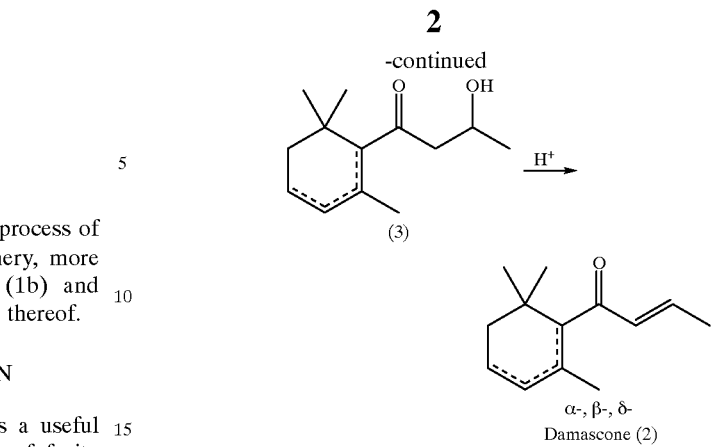

wherein any one of dotted lines means a double bond, which was reported by K. Subrahmania {J. C. S. Perkin 1, 1, 727(1975)}, is known as a process focusing on to the Aldol reaction of 2,6,6-trimethylcyclohexenyl methyl ketone (1).

2,6,6-Trimethyl-3-cyclohexenyl methyl ketone (1a), which is one of the starting materials of the above-described reaction, is synthesized by the Diels-Alder reaction between 1,3-pentadiene (4) and mesityl oxide (5) as shown in the following reaction scheme:

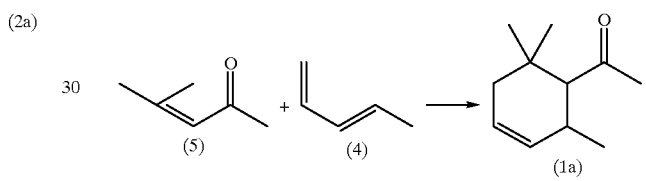

On the other hand, 2,6,6-trimethyl-2-cyclohexenyl methyl ketone (1b) is prepared by the following process, that is, by the Diels-Alder reaction of isobutene (6) and 4-methyl-3,5-hexadien-2-one (7).

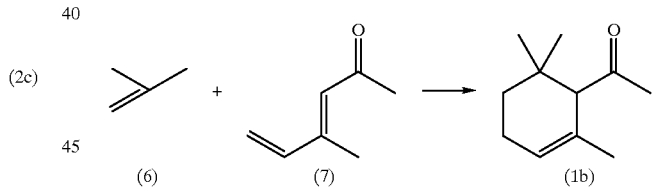

2,6,6-Trimethyl-1-cyclohexenyl methyl ketone (1c) is synthesized by the following reaction of ethylene (8) with 3-acetyl-2,4-dimethyl-1,3-pentadiene (9).

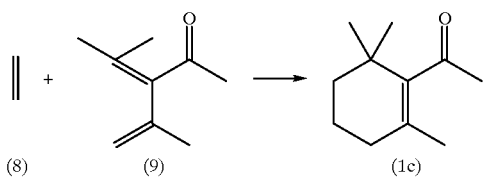

However, a process for synthesizing methyl-substituted-cyclohexenyl methyl ketones represented by the formulas (1b) and (1c) by isomerization of the double bond of the compound represented by the formula (1a) is not known yet.

Since α- and β-damascones which are typical fruity-floral fragrant materials are expensive, there is a demand for the development of a low-cost production process therefore.

The above-described production process of damascones by Subrahmania has a merit in its fewer production steps based on the Aldol reaction of 2,6,6-trimethylcyclohexenyl methyl ketones {(1b) and (1c)} with acetaldehyde. It is however difficult to industrially produce 4-methyl-3,5-hexadien-2-one (7) and 3-acetyl-2,4-dimethyl-1,3-pentadiene (9), the starting materials for the production of 2,6,6-trimethylcyclohexenyl methyl ketones {(1b) and (1c)}. Production of them also needs high costs. The above-described process is therefore not used industrially from the economical viewpoint. An object of the present invention is therefore to provide a more economical process for producing 2,6,6-trimethylcyclohexenyl methyl ketones {(1b) and (1c)}, that is, intermediates for the synthesis of α- and β-damascones.

SUMMARY OF THE INVENTION

Under the above-described conditions, the present inventors have carried out an extensive studies and, as a result, it has been found that methyl-substituted cyclohexenyl methyl ketones represented by (1b) and/or (1c), which are starting materials for the synthesis of α- and/or β-damascone, can be prepared economically by isomerization of methyl-substituted cyclohexenyl methyl ketone represented by the formula (1a).

In the present invention, there is thus provided a process for producing a 2-cyclohexenyl methyl ketone represented by the formula (1b), a 1-cyclohexenyl methyl ketone represented by the formula (1c), a trans-3-cyclohexenyl methyl ketone represented by the formula (1a'), or a mixture thereof, which comprises isomerizing, in the presence of an isomerizing catalyst, a 3-cyclohexenyl methyl ketone represented by the formula (1a).

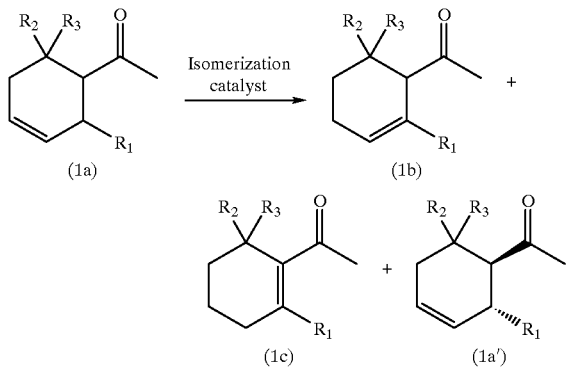

wherein, $R_1$, $R_2$ and $R_3$ each independently represents a hydrogen atom or a methyl group and at least two of $R_1$, $R_2$ and $R_3$ represent a methyl group.

DETAILED DESCRIPTION OF THE INVENTION

A novel production process of 2-cyclohexenyl methyl ketones (1b), 1-cyclohexenyl methyl ketones (1c), trans-3-cyclohexenyl methyl ketones (1a'), and mixture thereof according to the invention will next be described.

A 3-cyclohexenyl methyl ketone (1a), which is a starting material for the isomerization reaction of the invention, can be synthesized by the above-described reaction scheme, as reported, for example, by K. Subrahmania, et al., J. C. S. Perkin 1, 1, 727(1975), more specifically, by the Diels-Alder reaction between 1,3-pentadiene (4) and mesityl oxide (5) in the presence of an aluminum chloride catalyst.

Examples of the catalysts available for the isomerization reaction of the invention include acid catalysts such as hydrochloric acid, sulfuric acid, phosphoric acid, polyphosphoric acid, p-toluenesulfonic acid, Amberlist 15, Nafion H and activated clay; basic catalysts, for example, metal amide such as lithium diethylamide, sodium diethylamide and sodium cyclohexylamide, alkali metal hydroxides such as lithium hydroxide, potassium hydroxide and sodium hydroxide, alkali metal alcoholates such as potassium methoxide, catalysts having a transition metal (palladium, ruthenium or rhodium) which may be held on silica, alumina, silica alumina, zeolite or carbon, such as ruthenium chloride, rhodium chloride and phosphine complex catalysts of ruthenium or rhodium. Examples of the alkali metals in the alkali metal alcoholates include sodium, potassium and lithium, while those of the alkoxy group include methoxy, ethoxy, propoxy and tert-butoxy.

Although the reaction rate increases with the amount of the catalyst, use of 0.1 to 50 wt. % is preferred from the economical viewpoint. The reaction temperature varies depending on the catalyst, but usually ranges from 25 to 280° C.

This isomerization reaction can be allowed to proceed in a solventless manner, but it is possible to use a proper amount of a solvent. Examples of the solvent available here include hydrocarbons such as toluene and hexane, halogenated hydrocarbons such as dichloromethane, ethers such as tetrahydrofuran and methyl cellosolve, ketones such as acetone, esters such as ethyl acetate, alcohols such as ethanol, amines such as cyclohexyl amine, dimethyl sulfoxide, dimethylformamide and dimethylacetamide.

The reaction product obtained by this isomerization reaction usually contains an α-isomer {formula (1b)} having a double bond at the 2-position as a main component (65 to 99%), while it contains a β-isomer of the formula (1c) in an amount of 1 to 35%. They can be raw materials to produce fragrant materials in the form of a mixture, but can also be used after separation into each isomer by rectification such as distillation.

From 2,6,6-trimethyl-2-cyclohexenyl methyl ketone (1b, $R_1$, $R_2$ and $R_3$ each independently represents a methyl group) 2,6,6-trimethyl-1-cyclohexenyl methyl ketone (1c, $R_1$, $R_2$ and $R_3$ each independently represents a methyl group), trans-2,6,6-trimethyl-3-cyclohexenyl methyl ketone (1a', $R_1$, $R_2$ and $R_3$ each independently represents a methyl group), α-, β-, and δ-damascones can be produced by the above-described process of K. Subrahmania, et al.

That is, α-damascone is available by reacting 2,6,6-trimethyl-2-cyclohexenyl methyl ketone (1b) ($R_1$, $R_2$ and $R_3$ each independently represents a methyl group) with acetaldehyde to synthesize the corresponding Aldol product in the presence of an Aldol reagent prepared by an alkyl magnesium bromide (or chloride) and N-methylaniline (or another dialkylamine), and by dehydrating the resulting product by using a protonic acid such as PTS (p-toluenesulfonic acid) as a dehydration catalyst. In a similar manner, β-damascone is obtainable from 2,6,6-trimethyl-1-cyclohexenyl methyl ketone (1c), and δ-damascone is obtainable from trans-2,6,6-trimethyl-3-cyclohexenyl methyl ketone.

According to the isomerization reaction of the invention, a novel economical process for producing 2,6,6-trimethyl-2-cyclohexenyl methyl ketone (1b), 2,6,6-trimethyl-1-cyclohexenyl methyl ketone (1c), trans-2,6,6-trimethyl-3-cyclohexenyl methyl ketone (1a'), or mixture thereof can be provided. In addition, use of these compounds makes it possible to prepare α-, β-, δ-damascone at a lower cost. Moreover, mixtures containing essentially of α-, β-, δ-damascones are prepared at low cost.

The present invention will hereinafter be described in details by Examples. It should however be kept in mind that the present invention is not limited to or by them. In Examples, the below-described instruments were employed for the measurement of the physical properties of the compounds obtained in them.

NMR: DRX500 (Bruker)

GLC: HP5890 (Hewlett Packard) (Neutrabond-1, 30 m×0.25 mm×0.25 µm)

GC/MS: HP6890/5973 (Hewlett Packard) (HP-MS 60 m× 0.25 mm×0.25 µm)

REFERENTIAL EXAMPLE 1

Synthesis of 2,6,6-trimethyl-3-cyclohexenyl methyl ketone (1a)

In a 3-liter four-necked flask equipped with a dropping funnel, thermometer, condenser and a stirrer, placed were aluminum chloride (70 g) and toluene (300 ml) under ice cooling in a nitrogen gas stream. Under stirring, a solution of mesityl oxide (120 g) in toluene (300 ml) was added drop by drop during 1 hour at 2 to 5° C. After the addition, a solution of 1,3-pentadiene (450 g) in toluene (1,200 ml) was added drop by drop at 0 to −5° C. during 4 hours. After the addition, the mixture was stirred at the same temperature for 3 hours. After 3 hours at 30 to 40° C., the reaction was completed. The reaction mixture was cooled, followed by decomposition, washing with water (1,200 ml). After further washing with water (1,200 ml), the reaction mixture was washed with a 5% aqueous solution (500 ml) of sodium carbonate. Final washing with saturated salt solution (500 ml) gave a toluene solution of the product.

From the solution, toluene was removed by an evaporator, whereby an oil concentrate (390 g) was obtained. The resulting oil concentrate (390 g) was distilled through a Widmer spiral, whereby 127 g {b.p. 49 to 51° C./133 Pa (1 torr)} of 2,6,6-trimethyl-3-cyclohexenyl methyl ketone was obtained.

According to the gas chromatography of the distillate thus obtained, the content of the cis-isomer {cis-(1a)} was 94%, while that of the trans-isomer {trans-(1a)} was 6%. Each isomers exhibited the following spectral data.

Trans isomer

MS m/z; 166 (M+), 123, 109, 107, 81, 67, 55, 43

NMR [δ (CDCl$_3$)]; 5.55(1H,m), 5.46(1H,m), 2.54–2.45 (1H,m), 2.29(1H, d), 2.20(3H,s), 2.02–1.94(1H,m), 1.72–1.64(1H,m), 0.98(3H,s), 0.92(3H,s), 0.87(3H,d).

Cis isomer

MS m/z; 166 (M+), 138, 123, 109, 108, 95, 81, 69, 67, 55, 43

NMR [δ (CDCl$_3$)]; 5.72–5.68(1H,m), 5.43–5.39(1H,m), 2.59(1H,d), 2.52(1H,m), 2.19–2.11(1H,m), 2.11(3H,s), 1.70–1.63(1H,m), 0.95(6H), 0.92(3H,s)

EXAMPLE 1

{Synthesis of 2,6,6-trimethyl-2-cyclohexenyl methyl ketone (1b) and 2,6,6-trimethyl-1-cyclohexenyl methyl ketone (1c)}-1

In a 200-ml four-necked flask equipped with a thermometer, condenser and a stirrer, placed were 2,6,6-trimethyl-3-cyclohexenyl methyl ketone (10 g) synthesized in Referential Example 1, ethyl alcohol (40 ml) and rhodium trichloride trihydrate (0.9 g). Under stirring, they were reacted at 90° C. for 24 hours. The reaction mixture at this time was sampled and analyzed by gas chromatography, resulting in that the content of trans-2,6,6-trimethyl-3-cyclohexenyl methyl ketone was 11%, while those of 2,6,6-trimethyl-2-cyclohexenyl methyl ketone and 2,6,6-trimethyl-1-cyclohexenyl methyl ketone produced by the above reaction were 87% and 2%, respectively.

After the reaction, ethyl alcohol was distilled off by an evaporator. Toluene (50 ml) and water (250 ml) were added to wash the concentrate, followed by washing with saturated salt solution (50 ml). The toluene was then distilled off from the resulting toluene solution by an evaporator to yield an oil concentrate (11.2 g). This oil was distilled in a Claisen flask, whereby 8.1 g {(b.p.: 50 to 51° C./133 Pa (1 torr) of a mixture of trans-2,6,6-trimethyl-3-cyclohexenyl methyl ketone (1a') (10.5%), 2,6,6-trimethyl-2-cyclohexenyl methyl ketone (1b) (88.3%) and 2,6,6-trimethyl-1-cyclohexenyl methyl ketone (1c) (1.2%) were obtained.

MS data of 2,6,6-trimethyl-2-cyclohexenyl methyl ketone (1b)

m/z: 166 (M+), 123, 109, 95, 81, 67, 43

MS data of 2,6,6-trimethyl-1-cyclohexenyl methyl ketone (1c)

m/z: 166 (M+), 151, 123, 109, 95, 91, 81, 67, 43

EXAMPLE 2

{Synthesis of 2,6,6-trimethyl-2-cyclohexenyl methyl ketone (1b) and 2,6,6-trimethyl-1-cyclohexenyl methyl ketone (1c)}-2

In a 500-ml four-necked flask equipped with a thermometer, a condenser and a stirrer, placed were 2,6,6-trimethyl-3-cyclohexenyl methyl ketone (100 g) synthesized in Referential Example 1, tetraethyleneglycol monomethyl ether (150 ml), potassium t-butoxide (25 g) and tetra-n-butylammonium bromide (2 g). Under stirring, they were reacted at 175° C. for 4 hours. The reaction mixture at this time was sampled and analyzed by gas chromatography, resulting in that the content of trans-2,6,6-trimethyl-3-cyclohexenyl methyl ketone (1a') was 12%, while those of 2,6,6-trimethyl-2-cyclohexenyl methyl ketone (1b) and 2,6,6-trimethyl-1-cyclohexenyl methyl ketone (1c) produced by the above reaction were 61% and 27%, respectively.

After the reaction, the reaction mixture was distilled directly, whereby 93.5 g of a distillate was obtained. This distillate was rectified through a spinning band fractionating column having 200 theoretical plates, whereby 42 g of pure 2,6,6-trimethyl-2-cyclohexenyl methyl ketone (1b) (b.p. 70° C./5 torr) and 24 g of 2,6,6-trimethyl-1-cyclohexenyl methyl ketone (1c) {b.p. 71° C./655 Pa (5 torr)} free from an a-isomer were obtained.

EXAMPLE 3

{Synthesis of 2,6,6-trimethyl-2-cyclohexenyl methyl ketone (1b) and 2,6,6-trimethyl-1-cyclohexenyl methyl ketone (1c)}-3

In a 2,000-ml four-necked flask equipped with a thermometer, a condenser and a stirrer, placed were 2,6,6-trimethyl-3-cyclohexenyl methyl ketone (100 g) synthesized in Referential Example 1, dimethyl sulfoxide (1,500 ml) and potassium t-butoxide (35 g). Under stirring, they were reacted at 100° C. for 4 hours. The reaction mixture at this time was sampled and analyzed by gas chromatography, resulting in that the content of trans-2,6,6-trimethyl-3-cyclohexenyl methyl ketone (1a') was 4%, while those of the 2,6,6-trimethyl-2-cyclohexenyl methyl ketone (1b) and the 2,6,6-trimethyl-1-cyclohexenyl methyl ketone (1c) thus produced were 64% and 32%, respectively.

After the reaction, dimethyl sulfoxide was distilled off by an evaporator. Toluene (150 ml) and water (250 ml) were added to wash the concentrate, followed by washing with saturated salt solution (250 ml). The toluene was then distilled off from the resulting toluene solution by an evaporator to yield an oil concentrate (105 g) containing 2,6,6- trimethyl-2-cyclohexenyl methyl ketone (1b) and 2,6,6-trimethyl-1-cyclohexenyl methyl ketone (1c). This oil was distilled in a Claisen flask, whereby 85.5 g {(b.p. 50 to 55° C./133 Pa (1 torr)} of a 63:34 (%) mixture of 2,6,6-trimethyl-2-cyclohexenyl methyl ketone (1b) and 2,6,6-trimethyl-1-cyclohexenyl methyl ketone (1c) was obtained.

EXAMPLE 4

{Synthesis of 2,6,6-trimethyl-2-cyclohexenyl methyl ketone (1b) and 2,6,6-trimethyl-1-cyclohexenyl methyl ketone (1c)}-4

In a 500-ml four-necked flask equipped with a thermometer, a condenser and a stirrer, placed were 2,6,6-trimethyl-3-cyclohexenyl methyl ketone (10 g) synthesized in Referential Example 1, toluene (100 ml) and p-toluenesulfonic acid (2 g). Under stirring, they were reacted at 125° C. for 6 hours. The reaction mixture sampled at this time was analyzed by gas chromatography, resulting in that the content of trans-2,6,6-trimethyl-3-cyclohexenyl methyl ketone (1a') was 17%, that of 2,6,6-trimethyl-2-cyclohexenyl methyl ketone (1b) was 56.5%, and that of 2,6,6-trimethyl-1-cyclohexenyl methyl ketone (1c) was 26.5%.

Water (50 ml) was added to wash the reaction mixture, followed by washing with a 5% aqueous solution (50 ml) of sodium carbonate and then with saturated salt solution (50 ml). Toluene was then distilled off from the toluene solution by an evaporator, whereby an oil concentrate (10.3 g) was obtained. This oil was distilled in a Claisen flask, whereby 7.4 g {(b.p. 49 to 53° C./133 Pa (1 torr)} of a mixture of trans-2,6,6-trimethyl-3-cyclohexenyl methyl ketone (1a') (16%), 2,6,6-trimethyl-2-cycohexenyl methyl ketone (1b) (57%) and 2,6,6-trimethyl-1-cyclohexenyl methyl ketone (1c) (27%) was obtained.

REFERENTIAL EXAMPLE 2

{Synthesis of α-damascone}

In a 500-ml four-necked flask equipped with a thermometer, a condenser and stirrer, a solution of N-methylaniline (23.8 g) dissolved in 70 ml of toluene was added, in a nitrogen gas stream, to a tetrahydrofuran solution (82 ml) of ethyl magnesium bromide, which had been prepared from ethyl bromide (30.0 g) and magnesium (5.9 g) in 60 ml of tetrahydrofuran, while stirring under ice cooling. The N-methylaniline magnesium bromide solution thus freshly prepared was kept at 10 to 15° C., to which a solution, in toluene (37 ml), of 2,6,6-trimethyl-2-cyclohexenyl methyl ketone (1b) (37 g) synthesized in Example 2 was added drop by drop during 30 minutes, followed by stirring at the same temperature for 30 minutes. A solution of acetaldehyde (14.6 g) in toluene (15 ml) was then added drop by drop at −10 to 15° C. during 30 minutes. After completion of the addition, the reaction mixture was stirred for additional 90 minutes to complete the reaction.

While stirring under ice cooling, 3N hydrochloric acid (150 ml) was added to the reaction mixture to decompose and wash the same. The organic layer thus obtained was washed five times with 100 ml of 3N hydrochloric acid. After addition of p-toluenesulfonic acid (0.5 g) to the resulting toluene solution of an aldol compound {4-{2,6,6-trimethyl-2-cyclohexenyl)-4-oxobutan-2-ol}, the solution was heated. Under reflux of toluene, water generated by the dehydration reaction was separated. Dehydration reaction was thus completed. To the reaction mixture was added 50 ml of water to wash it, followed by washing with 50 ml of sodium bicarbonate solution and 50 ml of water. The organic layer thus obtained was concentrated by an evaporator to yield 45 g of an oil concentrate. This concentrate was distilled through a Widmer spiral, whereby 31 g of α-damascone {b.p. 105 to 106° C./160 Pa (1.2 torr)} was obtained.

REFERENTIAL EXAMPLE 3

{Synthesis of β-damascone}

In a similar manner to Referential Example 2 except for the use of the 2,6,6-trimethyl-1-cyclohexenyl methyl ketone (1c) synthesized in Example 2, reaction was carried out (but on a ½ scale throughout the reaction), whereby 13.7 g of β-damascone {b.p. 110 to 112° C./160 Pa (1.2 torr)} was obtained.

EXAMPLE 5

{Synthesis of 2,6,6-trimethyl-2-cyclohexenyl methyl ketone (1b) and 2,6,6-trimethyl-1-cyclohexenyl methyl ketone (1c)}-5

In a 100-ml four-necked flask equipped with a thermometer, a condenser and a stirrer, placed were 2,6,6-trimethyl-3-cyclohexenyl methyl ketone (10 g) synthesized in Referential Example 1, potassium methoxide (2.5 g), dimethyl sulfoxide (30 ml) and, as an internal standard substance for the analysis by gas chromatography, cyclododecane (3 g). The mixture was reacted at 120° C. for 2.5 hours. The reaction mixture was treated in an usual manner. Analysis by gas chromatography showed that the content of trans-2,6,6-trimethyl-3-cyclohexenyl methyl ketone was 4.4%, while those of 2,6,6-trimethyl-2-cyclohexenyl methyl ketone and 2,6,6-trimethyl-1-cyclohexenyl methyl ketone produced by the above reaction were 69.8% and 25.8%, respectively. As a result of calculation, the yield of the mixture of these three methyl ketones was found to be 8.6 g.

EXAMPLE 6

{Synthesis of 2,6,6-trimethyl-2-cyclohexenyl methyl ketone (1b) and 2,6,6-trimethyl-1-cyclohexenyl methyl ketone (1c)}-6

In a 100-ml four-necked flask equipped with a thermometer, a condenser and a stirrer, placed were 2,6,6-trimethyl-3-cyclohexenyl methyl ketone (10 g) synthesized in Referential Example 1, sodium methoxide (2.5 g), dimethyl sulfoxide (30 ml) and, as an internal standard substance for the analysis by gas chromatography, cyclododecane (3 g). They were reacted at 140 to 145° C. for 5 hours. The reaction mixture was treated in an usual manner. Analysis by gas chromatography showed that the content of trans-2,6,6-trimethyl-3-cyclohexenyl methyl ketone was 28.9%, while those of 2,6,6-trimethyl-2-cyclohexenyl methyl ketone and 2,6,6-trimethyl-1-cyclohexenyl methyl ketone produced by the above reaction were 49.2% and 21.9%, respectively. As a result of calculation, the yield of a mixture of these three methyl ketones was found to be 7.3 g.

EXAMPLE 7

{Synthesis of 2,6,6-trimethyl-2-cyclohexenyl methyl ketone (1b) and 2,6,6-trimethyl-1-cyclohexenyl methyl ketone (1c)}-7

In a 100-ml four-necked flask equipped with a thermometer, a condenser and a stirrer, placed were 2,6,6-trimethyl-3-cyclohexenyl methyl ketone (10 g) synthesized in Referential Example 1, sodium t-butoxide (2.5 g), dimethyl sulfoxide (30 ml) and, as an internal standard substance for the analysis by gas chromatography, cyclododecane (3 g). They were reacted at 120° C. for 4 hours. The reaction mixture was treated in an usual manner. Analysis by gas chromatography showed that the content of trans-2,6,6- trimethyl-3-cyclohexenyl methyl ketone was 52.3%, while those of 2,6,6-trimethyl-2-cyclohexenyl methyl ketone and 2,6,6-trimethyl-1-cyclohexenyl methyl ketone produced by the above reaction were 32.9% and 14.8%, respectively. As a result of calculation, the yield of a mixture of these three methyl ketones was found to be 9.1 g.

EXAMPLE 8

{Synthesis of 2,6,6-trimethyl-2-cyclohexenyl methyl ketone (1b) and 2,6,6-trimethyl-1-cyclohexenyl methyl ketone (1c)}-8

In a 100-ml four-necked flask equipped with a thermometer, a condenser and a stirrer, placed were 2,6,6-trimethyl-3-cyclohexenyl methyl ketone (10 g) synthesized in Referential Example 1, sodium ethoxide (2.5 g), dimethyl sulfoxide (30 ml) and, as an internal standard substance for the analysis by gas chromatography, cyclododecane (3 g). They were reacted at 130 to 140° C. for 6 hours. The reaction mixture was treated in an usual manner. Analysis by gas chromatography showed that the content of trans-2,6,6-trimethyl-3-cyclohexenyl methyl ketone was 34.7%, while those of 2,6,6-trimethyl-2-cyclohexenyl methyl ketone and 2,6,6-trimethyl-1-cyclohexenyl methyl ketone produced by the above reaction were 45.4% and 19.9%, respectively. As a result of calculation, the yield of a mixture of these three methyl ketones was found to be 6.9 g.

EXAMPLE 9

{Synthesis of 2,6,6-trimethyl-2-cyclohexenyl methyl ketone (1b) and 2,6,6-trimethyl-1-cyclohexenyl methyl ketone (1c)}-9

In a 100-ml four-necked flask equipped with a thermometer, a condenser and a stirrer, placed were 2,6,6-trimethyl-3-cyclohexenyl methyl ketone (10 g) synthesized in Referential Example 1, lithium t-butoxide (2.5 g), dimethylacetamide (30 ml) and, as an internal standard substance for the analysis by gas chromatography, cyclododecane (3 g). They were reacted at 140 to 145° C. for 6 hours. The reaction mixture was treated in an usual manner. Analysis by gas chromatography showed that the content of trans-2,6,6-trimethyl-3-cyclohexenyl methyl ketone was 30.2%, while those of 2,6,6-trimethyl-2-cyclohexenyl methyl ketone and 2,6,6-trimethyl-1-cyclohexenyl methyl ketone were 42.5% and 27.3%, respectively. As a result of calculation, the yield of a mixture of these three methyl ketones was found to be 5.3 g.

EXAMPLE 10

{synthesis of 2,6,6-trimethyl-2-cyclohexenyl methyl ketone (1b) and 2,6,6-trimethyl-1-cyclohexenyl methyl ketone (1c)}-10

In a 100-ml four-necked flask equipped with a thermometer, a condenser and a stirrer, placed were 2,6,6-trimethyl-3-cyclohexenyl methyl ketone (10 g) synthesized in Referential Example 1, potassium hydroxide (2.5 g), dimethyl sulfoxide (30 ml) and, as an internal standard substance for the analysis by gas chromatography, cyclododecane (3 g). They were reacted at 170 to 190° C. for 6 hours. The reaction mixture was treated in an usual manner. Analysis by gas chromatography showed that the content of trans-2,6,6-trimethyl-3-cyclohexenyl methyl ketone was 67.5%, while those of 2,6,6-trimethyl-2-cyclohexenyl methyl ketone and 2,6,6-trimethyl-1-cyclohexenyl methyl ketone produced by the above reaction were 20.1% and 12.4%, respectively. As a result of calculation, the yield of a mixture of these three methyl ketones was found to be 4.3 g.

EXAMPLE 11

{Synthesis of 2,6,6-trimethyl-2-cyclohexenyl methyl ketone (1b) and 2,6,6-trimethyl-1-cyclohexenyl methyl ketone (1c)}-11

In a 100-ml four-necked flask equipped with a thermometer, a condenser and a stirrer, placed were 2,6,6-trimethyl-3-cyclohexenyl methyl ketone (10 g) synthesized in Referential Example 1, sodium cyclohexylamide (3.5 g), cyclohexylamine (20 ml) and, as an internal standard substance for the analysis by gas chromatography, cyclododecane (3 g). They were reacted at 125 to 135° C. for 3 hours. The reaction mixture was treated in an usual manner. Analysis by gas chromatography showed that the content of trans-2,6,6-trimethyl-3-cyclohexenyl methyl ketone was 25.5%, while those of 2,6,6-trimethyl-2-cyclohexenyl methyl ketone and 2,6,6-trimethyl-1-cyclohexenyl methyl ketone were 48.6% and 25.9%, respectively. As a result of calculation, the yield of a mixture of these three methyl ketones was found to be 2.3 g.

While the invention has been described in detail and with reference to specific embodiments thereof, it will be apparent to one skilled in the art that various changes and modifications can be made therein without departing from the spirit and scope thereof.

This application is based on a Japanese patent application No. 2000-170823 filed on Jun. 7, 2000, the entire contents thereof being hereby incorporated by reference.

What is claimed is:

1. A process for producing a 2-cyclohexenyl methyl ketone represented by the following formula (1b):

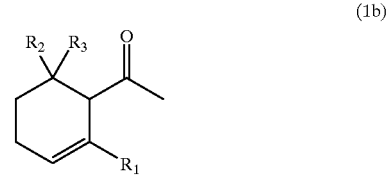

(1b)

wherein $R_1$, $R_2$ and $R_3$ each independently represents a hydrogen atom or a methyl group and at least two of $R_1$, $R_2$ and $R_3$ represent a methyl group, or a 1-cyclohexenyl methyl ketone represented by the following formula (1c):

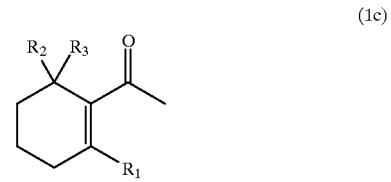

(1c)

wherein $R_1$, $R_2$ and $R_3$ have the same meanings as defined above, or a mixture of the cyclohexenyl methyl ketones of the formulas (1b) and (1c), which comprises isomerizing, in the presence of a catalyst, a 3-cyclohexenyl methyl ketone represented by the following formula (1a):

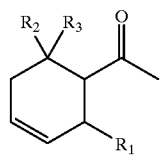

(1a)

wherein, $R_1$, $R_2$ and $R_3$ have the same meanings as defined above, and optionally distilling the mixture, wherein said catalyst is:
an acid catalyst; or
a basic catalyst, and wherein when said catalyst is said basic catalyst the isomerizing is conducted at a temperature of at least 100° C., wherein the basic catalyst is selected from the group consisting of potassium t-butoxide, potassium methoxide, sodium t-butoxide, sodium ethoxide, lithium t-butoxide, potassium hydroxide and sodium cyclohexylamide, and wherein the isomerizing is conducted in a solvent, and the solvent is selected from the group consisting of tetraethyleneglycol monomethyl ether, dimethyl sulfoxide, dimethylacetamide and cyclohexylamine.

2. A process of isomerizing, in the presence of a catalyst, a 3-cyclohexenyl methyl ketone represented by the following formula (1a):

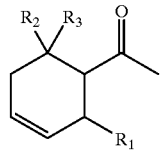

(1a)

wherein $R_1$, $R_2$ and $R_3$ each independently represents a hydrogen atom or a methyl group and at least two of $R_1$, $R_2$ and $R_3$ represent a methyl group, into a 2-cyclohexenyl methyl ketone represented by the following formula (1b):

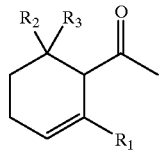

(1b)

wherein $R_1$, $R_2$ and $R_3$ have the same meanings as defined above, or a 1-cyclohexenyl methyl ketone represented by the following formula (1c):

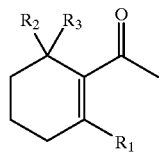

(1c)

wherein $R_1$, $R_2$ and $R_3$ have the same meanings as defined above, or a mixture of the cyclohexenyl methyl ketones of the formulas (1b) and (1c) and (1a'), wherein the cyclohexenyl methyl ketone of formula (1a') is the following trans 3-cyclohexenyl methyl ketone of formula (1a'):

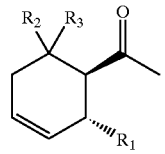

(1a')

wherein $R_1$, $R_2$ and $R_3$ have the same meanings as defined above, wherein said catalyst is:

an acid catalyst; or
a basic catalyst, and wherein when said catalyst is said basic catalyst the isomerizing is conducted at a temperature of at least 100° C., wherein the basic catalyst is selected from the group consisting of potassium t-butoxide, potassium methoxide, sodium t-butoxide, sodium ethoxide, lithium t-butoxide, potassium hydroxide and sodium cyclohexylamide, and wherein the isomerizing is conducted in a solvent, and the solvent is selected from the group consisting of tetraethyleneglycol monomethyl ether, dimethyl sulfoxide, dimethylacetamide and cyclohexylamine.

3. A process for producing a mixture consisting essentially of a trans-3-cyclohexenyl methyl ketone of formula (1a'):

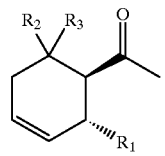

(1a')

wherein $R_1$, $R_2$, and $R_3$ each independently represents a hydrogen atom or a methyl group and at least two of $R_1$, $R_2$ and $R_3$ represent a methyl group, a 2-cyclohexenyl methyl ketone of formula (1b):

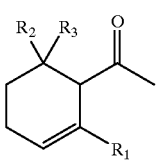

(1b)

wherein $R_1$, $R_2$ and $R_3$ have the same meanings as defined above, and a 1-cyclohexenyl methyl ketone of formula (1c):

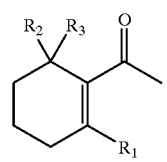

(1c)

wherein $R_1$, $R_2$ and $R_3$ have the same meanings as defined above, which comprises isomerizing, in the presence of a catalyst, a 3-cyclohexenyl methyl ketone represented by the following formula (1a):

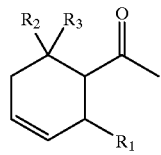

(1a)

wherein, $R_1$, $R_2$ and $R_3$ have the same meanings are defined above, wherein said catalyst is:

an acid catalyst; or a basic catalyst, and wherein when said catalyst is said basic catalyst the isomerizing is conducted at a temperature of at least 100° C., wherein the basic catalyst is selected from the group consisting of potassium t-butoxide, potassium methoxide, sodium t-butoxide, sodium ethoxide, lithium t-butoxide, potassium hydroxide and sodium cyclohexylamide, and wherein the isomerizing is conducted in a solvent, and the solvent is selected from the group consisting of tetraethyleneglycol monomethyl ether, dimethyl sulfoxide, dimethylacetamide and cyclohexylamine.

4. A process according to claim 1, wherein said catalyst is said basic catalyst and the temperature of the isomerizing is from 100° C. to 190° C.

* * * * *